United States Patent [19]

Heigel et al.

[11] 4,367,178

[45] Jan. 4, 1983

[54] PROCESS FOR THE PRODUCTION OF PURE LECITHIN DIRECTLY USABLE FOR PHYSIOLOGICAL PURPOSES

[75] Inventors: Walter Heigel, Ludwigshafen; Rolf Hueschens, Laatzen, both of Fed. Rep. of Germany

[73] Assignee: Kali-Chemie Pharma GmbH, Hanover, Fed. Rep. of Germany

[21] Appl. No.: 238,704

[22] Filed: Feb. 27, 1981

[30] Foreign Application Priority Data

Mar. 22, 1980 [DE] Fed. Rep. of Germany ....... 3011185

[51] Int. Cl.$^3$ .............................................. C11B 1/10
[52] U.S. Cl. ................................ 260/403; 260/412.4; 260/412.8
[58] Field of Search ................... 260/403, 412.4, 412.8

[56] References Cited

U.S. PATENT DOCUMENTS 3,923,847 12/1975 Roselius et al. .................. 260/412.4

FOREIGN PATENT DOCUMENTS 7207441 12/1972 Netherlands ..................... 260/412.4

*Primary Examiner*—John F. Niebling
*Attorney, Agent, or Firm*—Schwartz, Jeffery, Schwaab, Mack, Blumenthal & Koch

[57] ABSTRACT

Disclosed is a process for the production from raw lecithin of pure lecithin directly usable for physiological purposes, comprising the steps of contacting raw lecithin with gas as the extraction medium under supercritical conditions with respect to pressure and temperature in an extraction stage to produce a gas containing an extract; passing the gas containing the extract from the extraction stage into a separation stage; varying at least one of the pressure and the temperature of the gas in the separation stage to separate the extract-containing gas into the gas and the extract; recycling the gas after the step of varying the pressure and/or temperature; and removing pure lecithin from the extraction stage.

18 Claims, 1 Drawing Figure

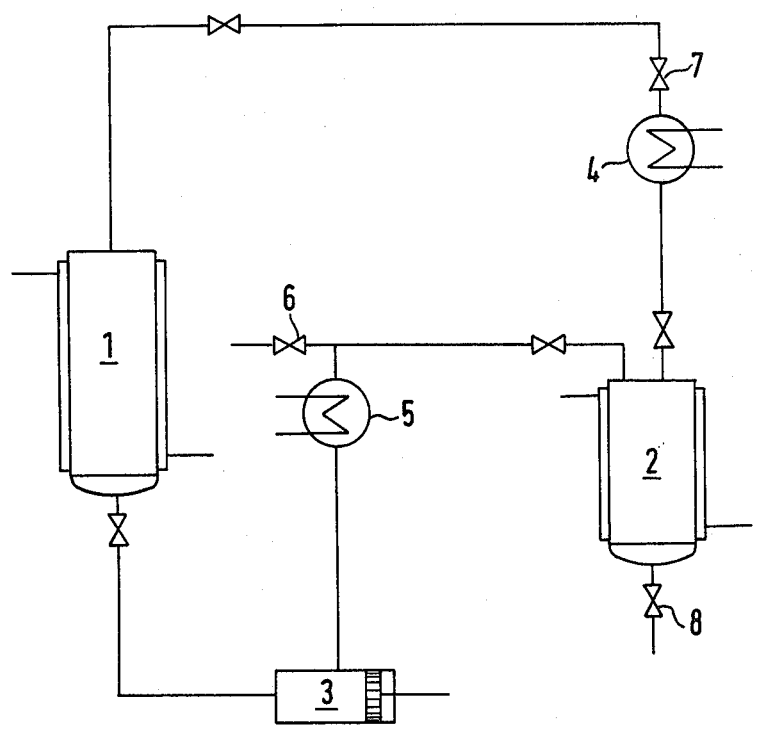

PROCESS FOR THE PRODUCTION OF PURE LECITHIN DIRECTLY USABLE FOR PHYSIOLOGICAL PURPOSES

BACKGROUND OF THE INVENTION

The present invention concerns a process for the production of pure lecithin, which is directly usable for physiological purposes, by extraction with supercritical gas.

The term lecithin designates a group of substances belonging to the series of phosphatides. These compounds, which contain the element phosphorus in the form of phosphate ester, may be obtained by the processing of certain vegetable and animal products containing fats.

The starting material for isolating, e.g., soy lecithin, is soy beans. Subsequent to cleaning, peeling and grinding the raw material, it is treated with solvents, and an oily product is obtained by extraction which contains lecithin in a colloidal solution. After additional treatment with water at elevated temperature and subsequent dehydration, the lecithin content of the solution is further enriched, whereby a semi-solid, pasty material is obtained, which is raw lecithin. It consists of approximately 60–70% phosphatides and approximately 30–40% oil components.

For the further processing and the technical utility of the lecithin, it is necessary to keep the oil component as low as possible. Since lecithins are used on a large scale in the production, processing and conservation of food items and also pharmaceutical and cosmetic preparations, exceedingly high requirements are established for the quality of the lecithins, in particular in relation to reservations as to physiological compatibility.

Heretofore, the oil content has been further reduced in costly purification processes, in part by boiling and evaporation or by means of further extraction with specific solvents and mixtures of solvents. These measures require either an additional subsequent, energy-intensive drying process, or else, in the case of the extraction method, residual parts of the solvents which are used in a large excess remain in the lecithin, so that again the traces of foreign solvents must be removed. In these processes, the lecithin is exposed over extended periods of time to stressful conditions, such as, for example, elevated temperatures, whereby the danger of ester cleavages or other decomposition processes is enhanced.

The present invention concerns a new process for the production of pure lecithin which is directly usable for physiological purposes, wherein raw lecithin is treated with gas as the means for extraction under conditions which are supercritical with respect to pressure and temperature, in accordance with a specific series of process steps.

Extraction processes operating with supercritical gases as the means for extraction are known. Thus, according to the process of German Pat. No. 21 27 618, extracts of hops are produced by extraction with supercritical gases. But in this process, resinous components, ethereal oils and acid contents are equally removed in a non-selective manner.

According to the process of East German Pat. No. 41 362, substances as unlike in their polarity as silicone oil, paraffin oil and aluminum-sec-butylate may be extracted together and simultaneously with non-polar supercritical gases.

According to the process of German Offenlegungsschrift No. 27 09 033, camomile is extracted with a supercritical gas. In this process again, the extract will contain in addition to the extracts desired, large components of undesirable accompanying substances, such as, for example, lipoids, dyestuffs or pigments, etc. The content of these components may be produced by a special, costly procedure to a slight extent, without however being able to significantly reduce the content of lipoid components.

SUMMARY OF THE INVENTION

It is therefore an object of the present invention to provide an improved process for the production of pure lecithin.

A further object of the invention resides in the provision of a process for producing pure lecithin which permits removal of oily components simply and at low cost.

It is also an object of the invention to provide such a process which is free of environmental pollution.

In accomplishing the foregoing objects, there has been provided in accordance with the present invention a process for the production from raw lecithin of pure lecithin directly usable for physiological purposes, comprising the steps of contacting raw lecithin with gas as the extraction medium under supercritical conditions with respect to pressure and temperature in an extraction stage to produce a gas containing an extract; passing the gas containing the extract from the extraction stage into a separation stage; varying at least one of the pressure and the temperature of the gas in the separation stage to separate the extract-containing gas into the gas and the extract; recycling the gas after the step of varying the pressure and/or temperature; and removing pure lecithin from the extraction stage. The process can be carried out either batchwise or continuously. Any physiologically compatible gas can be used as the extraction medium. One preferred gas is $CO_2$.

Further objects, features and advantages of the present invention will become apparent from the detailed description of preferred embodiments which follows, when considered together with the attached figure of drawing.

BRIEF DESCRIPTION OF THE DRAWING

The FIGURE of drawing is a schematic illustration of an arrangement of apparatus for carrying out the process according to the invention.

DETAILED DESCRIPTION OF PREFERRED EMBODIMENTS

It is entirely surprising and unexpected in view of the state of the art to find that it is possible to separate the oily accompanying substances from the lipoid lecithin completely by means of supercritical extraction.

In principle, all of the gases that are physiologically compatible and chemically inert with respect to lecithin may be used as the extraction medium, such as, for example, $CO_2$, $CHF_3$, $CF_3$—$CF_3$, $CHCl$=$CF_2$, $CF_2$=$CH_2$, $CF_3$—$CH_3$, $CHF_2$—$CH_3$, $CHF_2Cl$, $CF_3Cl$, $CF_2$=$CF_2$, $CF_2Cl_2$, $CCl_3$—$CHCl_2$, $C_3F_8$, $SF_6$, $N_2O$, $SO_2$, ethane, ethene, propane, propene, etc. or mixtures thereof. The use of $CO_2$ is particularly preferred.

In the extraction step, the substrate is exposed to the extraction medium under conditions wherein the gas is supercritical both with respect to temperature and pressure. The critical parameters of the abovementioned gases are sufficiently known.

In the case wherein $CO_2$ is used as the extraction-medium, the extraction is carried out at temperatures within the range of about 31.3° to 100° C., preferably from about 35° to 80° C., and in particular from about 40° to 60° C. and under pressures within the range of from about 72 to 800 bar, preferably from about 200 to 500 bar, and in particular from about 300 to 400 bar.

If an extraction medium other than $CO_2$ is used, the upper and lower limits of pressure and temperature for the extraction or separation, respectively, are determined by the corresponding critical data for that medium.

From the extraction stage, the extraction medium containing the extract is transferred to the separation stage to separate the extract from the extracting medium. The separation is effected by varying the temperature and/or the pressure, with preferably both parameters being changed.

If the temperature is to be varied, it is advantageous to lower the temperature. Preferably, the temperature is lowered under the critical temperature. Thus, for $CO_2$, for example, the temperature is lowered into a range of from about 10° to 32° C., particularly from about 15° to 25° C.

In the case of a variation of pressure, it is advantageous to lower the pressure. The pressure is thereby lowered below the critical pressure, in the case of $CO_2$, for example, to between about 10 and 72 bar, and preferably to between about 30 to 60 bar.

In a procedure as described hereinabove, the solubility of the extracted oily accompanying substances in the solvent is reduced by the changes in temperature and/or pressure to the extent that said substances precipitate from the extraction medium in the separation stage and may be removed during the extraction, for example, by a sluice, or after the extraction is completed.

The extraction medium is directly reusable without the need for labor- and energy-intensive purification, so that there are no additional emission problems. In order to again introduce the solvent into the extraction stage, it is merely necessary to place it into its supercritical state with respect to temperature and pressure, i.e., the change in temperature and/or pressure effected for the purpose of precipitation is reversed.

The lecithin purified of its accompanying substances (pure lecithin) may be taken from the extraction stage in a batch operation, following completion of the extraction. It is also possible, however, to remove the pure lecithin—for example by means of a sluice—in continuous operation during the extraction process. In both types of operation, extraction times of from about 1 to 12 hours, preferably from about 3 to 7 hours, are sufficient to obtain the end product in the purity desired.

The process according to the invention makes it possible therefore to obtain the desired product in a short period of time, while minimizing the expenditure for equipment, labor and energy and avoiding any pollution of the environment. The recirculation of the extraction medium in particular offers the possibility of automating the process, thereby effecting the extraction in a particularly economical manner. The pure lecithin obtained may be transferred directly to its use in foods, pharmaceuticals and cosmetics.

One embodiment of the process shall be explained in more detail hereinbelow with reference to the schematic representation contained in the FIGURE of drawing.

The substrate to be extracted (raw lecithin) is introduced into the extraction vessel 1. Subsequently, the extraction medium is added to the system by means of the inlet valve 6. It is not necessary to displace the air previously present in it. In the process, the extraction medium is compressed by the compressor 3 and likewise transported by it through the heat-exchangers 4 and 5 to the temperature desired in the respective individual process stages. The extraction stage 1 and the separation stage 2 are designed in the form of thermostatically-controlled pressure vessels, so that accurate control of the temperature in these process stages is feasible by means of supplemental thermostating.

When the pressures and temperatures desired in the individual stages are attained, the inlet valve 6 is closed and the extraction medium is placed in cirulation. The extraction medium brought to the extracting conditions by the heat exchanger 5 and the compressor 3 enters into intimate contact with the substrate in the extraction stage 1. The extraction medium containing the extract leaves this stage through a sieve device to prevent the entrainment of solid components into the separation stage, as well as clogging of valves, etc., and is passed through a throttle valve 7 by way of the heat-exchanger 4 into the separation stage 2, where the extract and the extraction medium separate. Whereas the latter is recirculated through the heat-exchanger 5 to the compressor 3, the extract is removed, either during the extraction through a sluice at the outlet 8 or following the completion of the extraction directly from the separation stage 2. Equally, the pure lecithin is taken from the extraction stage 1.

If, in place of a single pressure vessel 1, two or more pressure vessels are used, the process according to the invention can be readily operated in a continuous manner. In this case, pure lecithin can be continuously taken from one vessel in a manner known in itself and that vessel charged with a fresh supply of the substrate, while the extraction is proceeding in the other pressure vessel or vessels without interruption.

It is possible to connect the individual vessels in parallel or in series. In the latter case, it is particularly advantageous to effect the extraction "countercurrently", i.e., to charge the pressure vessel containing the substrate which has been extracted to the greatest extent with fresh extraction medium coming directly from the compressor 3 and to place the vessel containing the freshest substrate as the last element of the extraction stage.

The conditions of the process shall be demonstrated in detail in the following examples, which are merely illustrative and are not to be considered as limiting.

Extraction vessel:
  pressure $P_1$
  temperature $t_1$
Separation vessel:
  pressure $P_2$
  temperature $t_2$

EXAMPLE 1

1000 g of raw lecithin paste are filled into the extraction vessel, the vessel is closed and is extracted with $CO_2$ gas under supercritical conditions.

| | |
|---|---|
| $P_1$ = 400 bar | $P_2$ = 50 bar |
| $t_1$ = 60° C. | $t_2$ = 20° C. |
| extraction time: | 4 hours |

580 g of a solid, light yellow substance, the pure lecithin, is obtained. It is taken from the extraction vessel. From the separation vessel, 380 g of a yellow colored, clear oil is removed, together with a settled water phase of 30 g.

EXAMPLE 2

100 g of a raw lecithin paste with an oil content of approximately 30% are filled into the extraction vessel, the vessel is closed and extracted with supercritical carbon dioxide.

| | |
|---|---|
| $P_1$ = 300 bar | $P_2$ = 40 bar |
| $t_1$ = 40° C. | $t_2$ = 20° C. |
| extraction time: | 4 hours |

In the extraction vessel a residue of 69 g pure lecithin in the form of a solid, light yellow, nonhygroscopic substance remains. The separation vessel contains 31 g yellow colored, clear oil.

Thin layer chromatography shows that the products of both of the examples are free of oily components.

What is claimed is:

1. A process for the production of pure lecithin directly usable for physiological purposes by selective extraction from raw lecithin mixtures with oily substances, said process comprising the steps of:
   contacting said raw lecithin mixture with gas as the extraction medium under supercritical conditions with respect to pressure and temperature in extraction stage to produce a gas containing an extract;
   passing the gas containing the extract from the extraction stage into a separation stage;
   varying at least one of the pressure and the temperature of the gas in the separation stage to separate the extract-containing gas into the gas and the extract;
   recycling the gas after the step of varying the pressure and/or temperature; and
   removing pure lecithin from the extraction stage.
2. A process according to claim 1, wherein a physiologically compatible gas is used as the extraction medium.
3. A process according to claim 1, wherein the extraction medium is selected from $CO_2$, $CHF_3$, $CF_3-CF_3$, $CHCl=CF_2$, $CF_2=CH_2$, $CF_3-CH_3$, $CHF_2-CH_3$, $CHF_2Cl$, $CF_3Cl$, $CF_2=CF_2$, $CF_2Cl_2$, $CCl_3-CHCl_2$, $C_3F_8$, $SF_6$, $N_2O$, $SO_2$, ethane, ethene, propane, propene or a mixture thereof.
4. A process according to claim 1, wherein the extraction medium comprises $CO_2$.
5. A process according to claim 4, wherein the extraction stage is operated at a pressure between about 72 and 800 bar.
6. A process according to claim 4, wherein the extraction stage is operated at a pressure between about 200 and 500 bar.
7. A process according to claim 4, wherein the extraction stage is operated at a pressure between about 300 and 400 bar.
8. A process according to claim 4 or 5, wherein the extraction stage is operated at a temperature between about 31.3° and 100° C.
9. A process according to claim 4 or 5, wherein the extraction stage is operated at a temperature between about 35° and 80° C.
10. A process according to claim 4 or 5, wherein the extraction stage is operated at a temperature between about 40° and 60° C.
11. A process according to claim 1, wherein said varying step comprises a reduction in pressure and a reduction of temperature to less than critical conditions for the extraction medium.
12. A process according to claim 4, wherein the separation stage is operated at a pressure of between about 10 and 72 bar.
13. A process according to claim 4, wherein the separation stage is operated at a pressure of between about 30 and 60 bar.
14. A process according to claim 4, wherein the separation stage is operated at a temperature of from about 10° to 32° C.
15. A process according to claim 4, wherein the separation stage is operated at a temperature of from about 15° to 25° C.
16. A process according to claim 1, wherein the raw lecithin is extracted for a period of from about 1 to 12 hours.
17. A process according to claim 1, wherein the raw lecithin is extracted for a period of from about 3 to 7 hours.
18. A process according to claim 1, which is carried out continuously.

* * * * *